United States Patent [19]
Bloomberg et al.

[11] Patent Number: 5,922,698
[45] Date of Patent: Jul. 13, 1999

[54] PESTICIDAL FORMULATION METHOD OF COMBATING PESTS

[75] Inventors: Martin David Bloomberg; Coenraad Jacobus Beukes Scholtz; Ian Francois Brink, all of Johannesburg, South Africa

[73] Assignee: Gouws & Scheepers (Proprietary) Limited, South Africa

[21] Appl. No.: 08/273,639

[22] Filed: Jul. 12, 1994

Related U.S. Application Data

[62] Division of application No. 07/900,178, Jun. 17, 1992, abandoned.

[30] Foreign Application Priority Data

Jun. 18, 1991 [ZA] South Africa .......................... 91/4674

[51] Int. Cl.$^6$ .......................... A01N 57/10; A01N 57/26; A01N 57/28; A01N 25/02
[52] U.S. Cl. .......................... 514/137; 514/772; 514/937; 514/941; 514/972; 514/975; 514/946; 424/405; 424/DIG. 8
[58] Field of Search .................................... 214/118, 137, 214/972, 772, 937, 941, 975, 946; 424/405, DIG. 8

[56] References Cited

U.S. PATENT DOCUMENTS

| | | | |
|---|---|---|---|
| 3,309,266 | 3/1967 | Magee | 514/137 |
| 3,676,555 | 7/1972 | Schrader | 514/137 |
| 3,689,604 | 9/1972 | Schrader | 558/199 |
| 3,988,351 | 10/1976 | Copes | 504/129 |
| 4,105,780 | 8/1978 | Berkelhammer | 549/447 |
| 4,948,787 | 8/1990 | Chen | 514/141 |
| 5,185,353 | 2/1993 | Turnbull | 514/364 |
| 5,798,346 | 8/1998 | Bloomberg et al. | 514/137 |

FOREIGN PATENT DOCUMENTS

| | | |
|---|---|---|
| 0015749 | 9/1980 | European Pat. Off. . |
| 3116016 | 11/1982 | Germany . |
| 3317399 | 1/1984 | Germany . |
| 0161047 | 8/1984 | Germany . |
| 0235019 | 4/1986 | Germany . |

OTHER PUBLICATIONS

The Agrochemicals Handbook, 2d ed., 1987, The Royal Socieity of Chemistry, England, p. A265/Aug. 1987.

Ware, George W., "Complete Guide to Pest Control—With and Without Chemicals," Thomson Publicatons, Fresno (CA), p. 27.

Reort by Dept. of Entomology of South Africa Citrus Exchange 1990 (Paragraph Bridging pp. 50–51).

The Merck Index, 10th ed. Merck Co., Inc. Rahway, N.J., 1983, p. 644.

*Primary Examiner*—John Pak
*Attorney, Agent, or Firm*—Ladas & Parry

[57] ABSTRACT

The invention relates to a pesticidal formulation having systemic activity and intended for application to a stem of a plant, which includes the compound methamidophos as an active ingredient, a suitable solvent for the active ingredient, and a colorant selected to impart an identifiable coloration to the formulation for a predetermined period of time related to the duration of the residual activity of the active ingredient. The solvent is preferably a non-volatile organic solvent selected for its low phytotoxicity and its low toxicity for humans, such as an aryl ethoxylate or a polyhydric alcohol. The colorant is preferably selected on the basis of its water solubility, having a limited solubility in water to be eluted gradually from the formulation over a period of time selected to coincide with the duration of the residual activity of the active ingredient. The formulation advantageously also includes an ingredient capable of screening ultra violet rays of the sun.

46 Claims, No Drawings

5,922,698

PESTICIDAL FORMULATION METHOD OF COMBATING PESTS

This is a divisional of application Ser. No. 07/900,178 filed on Jun. 17, 1992 now abandoned.

THIS INVENTION relates to a pesticidal formulation, and to a method of selectively combating or controlling pests on plants and trees without adversely affecting the plants and trees themselves and the beneficial insects present on the plants and trees.

More particularly the invention relates to such a pesticidal formulation and method which are particularly suitable to be used in a stem treatment for citrus and other fruit trees, including subtropical fruit trees as well as deciduous fruit trees and vines, and ornamental trees and shrubs, for combating or controlling undesirable insects and other pests, while displaying little or no phytotoxic side effects.

According to the invention there is provided a pesticidal formulation having systemic activity and intended for application to a stem of a plant, which includes the compound methamidophos as an active ingredient, and a selected solvent for the active ingredient, the solvent being selected for its low volatility, low phytotoxicity and low toxicity for humans, and its good penetrative ability.

The Applicant has found that the formulation may advantageously also include a colorant selected to impart an identifiable coloration to the formulation for a predeterminable period of time related to the duration of residual activity of the active ingredient.

The formulation according to the invention is intended to be applied as a stem application to the trunks, stems or branches of trees and plants infested with pests, including undesired insects and acarides, to combat or control such pests by systemic action, and the words "for application to a stem of a plant" should be interpreted accordingly.

The formulation according to the invention may thus be used as what is referred to in the an as a stem paint. The active ingredient has a systemic efficacy, and by applying the formulation to the trunk, stem or branch of a tree or plant, the active ingredient will selectively target sucking insects or other eating pests infesting the tree or plant in remote localities eg on the growth ends, leaves or fruit, and will not adversely affect the beneficial predator and parasite complex which preys on these pests, and will moreover display little or no phytotoxic effect on the tree or plant itself.

The term "methamidophos" is the common name used for the chemical compound O,S-dimethyl phosphoramidothioate. A practical advantage of this compound when used in accordance with the invention, is its relatively high solubility in water, in contrast to the relative insolubility of other organophosphates. This has the beneficial effect that the active ingredient will readily be taken up in the protoplasmic fluids of the plants or trees, and will be transported relatively quickly to, and become available at, remote localities, such as growth points, where pesticidal infestation occurs.

However, to provide a formulation with methamidophos as the active ingredient and which will not have a phytotoxic effect when applied as a stem application to the trunks, branches or stems of trees such as citrus trees, subtropical fruit trees, deciduous fruit trees and vines, and ornamental trees and shrubs, the Applicant has found that it is essential for the methamidophos to be combined with a specially selected suitable solvent.

The active ingredient methamidophos has been used as a foliar application on a wide range of crops for the control of a broad spectrum of insects, as a 585 g/l water soluble liquid formulation. However, on citrus and other fruit trees, including subtropical and deciduous fruit trees, the results achieved with known formulations containing methamidophos have been disappointing and inadequate, and in some cases disastrous.

The usage of known methamidophos formulations on deciduous fruit is in practice restricted to peaches only, due to phytotoxicity. Also on citrus trees results with known formulations of methamidophos have been unsatisfactory.

Certain rootstocks that are used in the citrus industry are extremely susceptible to stern applications of pesticides. For example, the use of formulations with monocrotophos as the active ingredient, on the susceptible Volka rootstocks has resulted in severe phytotoxicity. This phytotoxicity can take the form of either bark split or gummosis. In trials conducted on Volka rootstock with a formulation containing methamidophos (585 g/l) in an isopropyl alcohol solvent, severe phytotoxic symptoms were recorded.

Growers who had tried the product methamidophos in an isopropyl alcohol (585 g/l) as a stem treatment to young citrus trees, found that the treatment resulted in the death of the treated plants.

The Applicant has found that the selection of a suitable solvent makes it possible for methamidophos to be incorporated into a formulation which is versatile and specifically suitable for use on citrus and fruit trees, including subtropical and deciduous fruit trees, vines, and ornamental trees and shrubs, and which has increased efficacy in combating various pests infesting these trees, and good penetration ability and which moreover has little or no phytotoxicity or toxicity towards humans.

The solvent may preferably be a non-volatile organic solvent selected for its low phytotoxicity and its low toxicity for humans. It has been found that a non-ionic surfactant, such as an aryl ethoxylate or an alkyl-substituted aryl ethoxylate, gives particularly good results as a solvent in practice. Such a surfactant displays substantially no phytotoxicity, achieves better penetration of the active ingredient into the bark and stem of the trees or plants and at the same time allows only limited penetration into human skin. Such a surfactant will also enhance the uptake of the formulation into the protoplasmic fluids of the plants or trees, thereby reducing the time delay before the active ingredient becomes effective at the infested locality. Polyhydric alcohols such as glycerol, also give favourable results. Being natural products, they display substantially no phytotoxicity, and they are less toxic to human subjects involved with the application of the formulation. Other suitable solvents may for example be hexylene glycol, ethoxylated alkylphenols, ethoxylated propyleneoxide polymers, polypropylene glycol, or polyethylene glycol. Of all of theses aryl ethoxylates or aryl-substituted aryl ethoxylates and polyhydric alcohols are preferred because of their relatively low phytotoxicity and low toxicity for humans.

For example, the substitution of isopropyl alcohol with hexylene glycol as the solvent in the formulation containing 585 g/l of methamidophos resulted in a marked reduction in phytotoxic symptoms. Particularly where a polyhydric alcohol or an aryl ethoxylate was used as a solvents no phytoxicity was found on susceptible Volka citrus rootstock.

From field trials (as set out more fully further below), it was evident that the choice of solvent in the methamidophos formulation can have a marked effect on both the degree of plant tolerance and safety as well as the rate of uptake of the systemic insecticide by the plant. While the glycols improve the safety of the product, it would appear that the use of an aryl ethoxylate solvent or equivalent thereof can enhance insecticidal efficacy without sacrificing plant tolerance.

The solvent should preferably be selected to have a low volatility, so as to reduce the formation of vapours and fumes rising up into the lower canopy of leaves and foliage of the trees and plants, thus reducing adverse effect on beneficial insects inhabiting the foliage. It would be evident that a low volatility solvent would also reduce inhalation of fumes and vapours by human subjects applying the formulation. The formulation as provided by the invention accordingly entails advantages of comparative safety to warm-blooded animals and humans, as wel as to beneficial insects inhabiting the trees.

The solvent which is particularly preferred by the Applicant, is nonyl phenol ethoxylate. This compound is commercially available as one of the SYNPERONIC NP range of products (commercial name of and supplied by ICI Industrial Chemicals and Colours) particularly the grade containing between 6–13 mols, preferably about 9 mols of ethylene oxide of nonyl phenol ethoxylate is suitable. Another preferred solvent is octyl phenol ethoxylate, which is commercially available as part of the SYNPERONIC OP range also supplied by and of ICI.

Polyhydric alcohols that have been found to give satisfactory results, are hexylene glycol and glycerol.

It is also envisaged that a combination of solvents may be used, eg an aryl ethoxylate surfactant in combination with glycerol, to provide a formulation with a suitable viscosity and applicability at a temperatures. If necessary, an ingredient may be incorporated to modify the viscosity of the formulation, where this is required to suit different conditions.

The incorporation in the formulation of a colorant as set out herein, namely a colorant which will impart an identifiable coloration to the formulation for a period of time related to the duration of the residual activity of the active ingredient methamidophos, is of particular practical importance. Methamidophos is listed as what is referred to in South African legislation as a Schedule B1 poison. As such, a prescribed safety harvest interval is required between the date of last application to crops and the date of harvesting the crops. The safety harvest interval is determined on the basis of the level of active ingredient present in the edible crop. The tolerance Revels allowed may vary widely for different chemical substances, and a specific safety harvest interval must be determined for a particular chemical formulation. With a formulation containing methamidophos in the concentrations referred to herein; a safety harvest interval of 21 days has for example been approved in citrus.

It will be evident that the presence of a colorant as envisaged by the Applicant would assist a user of the formulation to determine when the safety harvest interval has elapsed. With reference to the coloration imparted by the colorant, a user may minimise the risk of too frequent or too many applications of the formulation within a recommended application interval (which would result in the level of active ingredient exceeding the applicable tolerance level). Similarly, reference to the coloration would avoid the risk of harvesting the crop before the safety harvest interval has elapsed.

The colorant may be a specific dye or pigment selected to impart identifiable and visible coloration to the formulation for the particular period of time, which period is related to the duration of the residual activity of the active ingredient. Thus, the colorant may advantageously be selected to provide a visible and identifiable coloration to the formulation as long as the effective residual activity of the active ingredient endures. This period may be determined empirically and with reference to the relevant safety harvest interval. At the end of the relevant period, the colorant may lose or change its color, or may itself disappear or be eluted from the formulation, to indicate that a new application of the formulation is necessary, or that the edible crop may be harvested.

A dye or pigment colorant may be selected on the basis of its water solubility. For example, a colorant may have a limited solubility in water, so that it will gradually be eluted from the formulation by moisture present in the environment over a predeterminable period of time. At a given point, (e.g., when the colorant has been entirely removed) the colour change observed in the formulation may be indicative of the fact that the activity of the formulation has been spent and that a fresh application is necessary.

The dye or pigment colorant may also be selected to display a color change in response to other conditions, (e.g., the pH of the formulation or the environment where the formulation is used).

It will be evident at the presence in the formulation of such a colorant with a distinctive and visible colour, would in practice serve as an indication of the trees or plants &at have already been treated, to distinguish them from those that are still to be treated. Furthermore ore as a result of the colour change achieved, an indication will be given of when a fresh application of the formulation is required. Its practical utility in the context of the safety harvest interval has already been set out.

Suitable dye colorants to be used in accordance with the invention are oil dyes. Of these, the colorant commercially available as Waxoline Blue is preferred. This colorant is commercially available from ICI (industrial Chemicals and Colours). it has been found that the incorporation of between about 0.35–0.7% by weight, preferably about 0.4% by weight, of Waxoline Blue in a formulation according to the invention gives satisfactory results in practice.

According to a further feature of the invention the formulation may also include a substance capable of screening or absorbing ultra violet rays of The sun. The Applicant believes that sunlight may have the effect of degrading the organophosphate active ingredient, and that an ultra violet (UV) screen or absorber will reduce such degradation, and thus extend the residual activity of the active ingredient.

As pointed out above, it has been found that certain of the solvents and/or the active ingredient may in some cases have an injurious effect on the trees or plants being treated, eg in the case of deciduous fruit trees for example by burning or injuring the outer bark layers. The applicant believes that a UV screen or absorber will have the further effect of preventing or at least reducing further damage by the sun to an already sensitive area on the trunk or stem of a tree. Thus, the Applicant believes that a UV screen or absorber will act in synergism with the other ingredients of the formulation to prevent or reduce injury to the trees or plants, and where injury has occurred, to prevent or reduce aggravation of such injury by the sun. Cracking or blistering of the bark of trees treated may thus be prevented or reduced.

Suitable UV screens or blocks may be ethoxylated p-aminobenzoic acid, benzotriazole, benzophenone, the product TINUVIN commercially supplied by Ciba-Geigy, and the product UNIVUL commercially supplied by Badische Anilin- und Sodafabrik (BASF). However, other substances known to screen or block ultra violet rays may also be used. From about 0.1% by weight or more, conveniently between about 2–3% by weight, of UV block may be incorporated in the formulation.

The formulation according to the invention may be made up particularly for citrus and other fruit trees, including subtropical fruit trees, deciduous fruit trees, vines, and ornamental trees and shrubs, and may conveniently be provided in the form of a concentrate, to be used as is, incorporating between about 400 g/l and 600 g/l, based on the total volume of the product, of the active ingredient dissolved in a solvent which may be an aryl ethoxylate such as nonyl phenol ethoxylate, or a polyhydric alcohol such as hexylene glycol. It has been found that a formulation containing 500 g/l, based on the total volume of the product, of active ingredient in nonyl phenol ethoxylate as the solvent produces a product with a satisfactory level of activity and substantially no phytoxicity, particularly suitable for use on citrus trees as a stem application.

The invention extends also to a method of combating or controlling pests on trees and plants, particularly citrus trees, subtropical and deciduous fruit trees and vines, which includes the step of applying, (e.g., by painting), the formulation according to the invention to the trunk, stem or branch of a tree or plant to be treated. The formulation may conveniently be applied in the form of a band and the band may advantageously encircle such stem or branch. Its width my correspond roughly to the diameter of the treated trunk, stem or branch. It will be appreciated that the width of the band will determine the quantity of active ingredient applied and thus its Revel of activity. Alternatively, the formation may be applied in one or more vertical strips or in the form of dots or blotches on the trunk or stem to be treated.

It should be understood that once the identifiable coloration of the formulation has disappeared or changed, a fresh application of the formulation may be made.

For use as a stem application the formulation may be provided in the form of a concentrate, to provide a stem paint with a suitable concentration of active ingredient. The invention thus extends also to a stem paint for application to the trunks, stems or branches of trees and plants by means of a brush or roller or a suitable applicator such as a modified pesticide applicator. The stem paint application may be formulated to be particularly applicable to citrus trees, subtropical and deciduous fruit trees, ornamentals and shrubs and vies.

The formulation according to the invention has been found to be effective inter alia against mites (including red mites (*Panonychus citri*) and bud mites (*Aceria sheldoni*)) aphids (*Toxoptera spp*) and psylla (*Trioza erythreae*), thrips (*Thripidae spp*), certain scale, mealy bug (*Pseudococcidae spp*, eg planococcus spp), Australian bug (*Icerya purchasi*), and various caterpillar pests in citrus (eg orange dog (*Papilio spp*), American bollworm (*Heliothis armijera*)).

The invention and the manner in which it may be put into practice will now be further elucidated by way of the following Examples, based on field trials carried out with a formulation according to the invention.

EXAMPLE I

A basic formulation comprising methamidophos as the active ingredient in hexylene glycol as the solvent was made up in a concentration of 500 g/l of total product. The formulation was applied to 5 citrus trees selected at random the trees being 20 year old Valencias with a stem diameter of about 170 mm. A single replicate was randomly selected as a control for each of the 5 trees treated.

The formulation was applied undiluted to the test trees as a stern paint, in the form of a band encircling the stem and having a width corresponding approximately with the stem diameter.

Five shoots from each tree were removed and examined microscopically for the presence of bud mite. Five axils per shoot were examined (25 axils per tree/rep) for the presence of mite. The assessment was made 19 days after the application. The results are set out in Table 1.

TABLE 1

EFFICACY OF FORMULATION ON BUD MITE ON CITRUS 19 DAYS AFTER APPLICATION (19DAA)

% AXILS INFECTED WITH MITE

|  | i | ii | iii | iv | v | Mean % | % EFFICACY |
|---|---|---|---|---|---|---|---|
| UNTREATED | 84 | 52 | 72 | 76 | 72 | 71.2 |  |
| TREATED | 0 | 4 | 0 | 0 | 0 | 0.8 | 98.9 |

The actual findings on the axils examined are set out in Table 2.

TABLE 2

NUMBER OF BUD MITE-INFESTED AXILS PER BRANCH (5 AXILS/BRANCH) 19DAA

| | UNTREATED CONTROL | | | | | TREATED TREES | | | | |
|---|---|---|---|---|---|---|---|---|---|---|
| | Tree 1 | T2 | T3 | T4 | T5 | Tree 1 | T2 | T3 | T4 | T5 |
| Tree 1 | 4/5 | 2/5 | 5/5 | 5/5 | 5/5 | 0/5 | 0/5 | 0/5 | 0/5 | 0/5 |
| Tree 2 | 3/5 | 3/5 | 1/5 | 4/5 | 2/5 | 0/5 | 0/5 | 0/5 | 1/5 | 0/5 |
| Tree 3 | 5/5 | 3/5 | 5/5 | 2/5 | 3/5 | 0/5 | 0/5 | 0/5 | 0/5 | 0/5 |
| Tree 4 | 4/5 | 2/5 | 3/5 | 5/5 | 5/5 | 0/5 | 0/5 | 0/5 | 0/5 | 0/5 |
| Tree 5 | 5/5 | 2/5 | 3/5 | 5/5 | 3/5 | 0/5 | 0/5 | 0/5 | 0/5 | 0/5 |

ASSESSMENT

The application of a formulation according to the invention as a stern treatment to 20 year old Valencias gave excellent control of a high infestation of bud mite present on the terminal growth of the treated trees some three weeks after application.

EXAMPLE II

Objective: To determine the ability of various methamidophos containing formulations to protect new growth against citrus thrip (*S. aurantii*) damage, when applied as a trunk treatment Locality: "Sunningdale Estates" Potgietersrus, Transvaal, Republic of South Africa Crop: Citrus Variety: Navels Application Dates: 26-2-1992; 13-3-1992

Assessment Date: 23-3-1992

Trial Design: Random block; 4 trees per replicate; 4 replicates

| PRODUCT | ACTIVE INGREDIENT | SOLVENT |
|---|---|---|
| Formulation 1* | methamidophos 500 g/l | Hexylene glycol |
| Formulation 2* | methamidophos 500 g/l | Polyhydric alcohol |
| Formulation 3* | methamidophos 500 g/l | Aryl ethoxylate |

*All three formulations included as a colorant 0.38% by weight of Waxoline Blue.

RESULTS

TABLE 3

Efficacy of methamidophos formulations against thrip damage on new growth

| | Number of new shoots per replicate (4 trees) | | | | |
|---|---|---|---|---|---|
| Product | i | ii | iii | iv | Mean |
| Untreated | 0 | 12 | 0 | 0 | 3 |
| Formulation 1 | 67 | 87 | 102 | 90 | 86.5 |
| Formuiation 2 | 19 | 103 | 89 | 96 | 76.8 |
| Formulation 3 | 117 | 217 | 92 | 87 | 128.3 |

ASSESSMENT

Thrip feeding damage on young growth can cause malformation of emergent flush, and in many situations is so severe that the growth flush can be severely retarded.

Dependent on locality and variety, the number of growth flushes can vary between 4 and 6 per season. It is during these periods of flushing that new growth is set which forms the basis of the following season's crop. Any form of management which protects new growth from thrip feeding damage, allowing young shoots to develop, will ultimately result in more vigorous growth, bigger canopy and higher yields.

From the results obtained above it is evident that the thrip feeding damage was extremely severe, as indicated by the lack of new shoots recorded in the untreated plots.

All methamidophos-containing treatments provided protection of the new Bush against drip damage.

The trees treated with Formulation 3 exhibited a markedly higher number of new shoots following two treatments, when compared to the remaining formulations.

In this trial the number of shoots recorded on the trees treated with Formulation 2 were similar to that of the trees treated with Formulation 1.

EXAMPLE III

Objective: To determine the ability of various methamidophos containing formulations to protect new growth against citrus thrip (*S. aurantii*) damage, when applied as a trunk treatment Locality: "Jassi" Letsitele, Northern Transvaal, Republic of South Africa Crop: Citrus Variety: Grapefruit, Star Ruby Application Dates: Oct. 3, 1992; 31-3-1992
Assessment Date: 31-3-1992
Trial Design: Random block; 10 trees per treatment.

TREATMENTS

| PRODUCT | ACTIVE INGREDIENT | SOLVENT |
|---|---|---|
| Formulation 1* | methamidophos 500 g/l | Hexylene glycol |
| Formulation 2* | methamidophos 500 g/l | Polyhydric alcohol |
| Formulation 3* | methamidophos 500 g/l | Aryl ethoxylate |

*All three formulations included as a colorant 0.38% by weight of Waxoline Blue.

RESULTS

TABLE 4

Efficacy of methamidophos formulations against thrip damage on new growth

| | Number of new shoots per replicate (4 trees) | | | | | | | | | | |
|---|---|---|---|---|---|---|---|---|---|---|---|
| Product | i | ii | iii | iv | v | vi | vii | viii | ix | x | Mean |
| Untreated | 64 | 4 | 0 | 1 | 10 | 23 | 25 | 17 | 22 | 10 | 17.6 |
| Formulation 1 | 326 | 338 | 140 | 288 | 152 | 178 | 110 | 212 | 237 | 347 | 232.8 |
| Formulation 2 | 290 | 185 | 280 | 164 | 252 | 486 | 385 | 214 | 209 | 468 | 293 |
| Formulation 3 | 319 | 186 | 366 | 252 | 138 | 148 | 298 | 212 | 331 | 129 | 237.9 |

ASSESSMENT

Thrip feeding damage on young growth in citrus on this estate is such that the majority of emergent growth points either do not produce a flush or are severely misformed.

This level of feeding damage can retard growth quite markedly, resulting in a reduction in canopy size and suboptimal fruit bearing.

The number of new shoots recorded in the untreated trees was significantly lower than that in the methamidophos treated plots. Those shoots that did emerge were misformed due to feeding damage.

The methamidophos-containing treatments provided protection of the new flush against thrip damage.

The trees treated with Formulation 2 exhibited a higher number of new shoots following a single application, when compared to the remaining formulations.

In this trial the number of shoots recorded in the plots treated with Formulation 3 were similar to that recorded from the trees treated with Formulation 1.

EXAMPLE IV

Objective: To determine the insecticidal efficacy of various methamidophos-containing formulations against citrus aphid when applied as trunk treatments Locality: Nelspruit, Eastern Transvaal, Republic of South Africa Crop: Citrus Variety: Navels Trial Design: Completely randomised. Infested new growth points

TREATMENTS

| PRODUCT | ACTIVE INGREDIENT | SOLVENT |
| --- | --- | --- |
| Formulation 1* | methamidophos 500 g/l | Hexylene glycol |
| Formulation 2* | methamidophos 500 g/l | Polyhydric alcohol |
| Formulation 3* | methamidophos 500 g/l | Aryl ethoxylate |

*All three formulations included as a colorant 0.38% by weight of Waxoline Blue.

RESULTS

TABLE 5

Efficacy of methamidophos formulations against aphid on new growth

| PRODUCT | Time lapse after application for effect on aphids |
| --- | --- |
| Formulation 1 | 24 hours |
| Formulation 2 | 24 hours |
| Formulation 3 | 8–10 hours |

ASSESSMENT

The choice of solvent used in the methamidophos formulation and its influence on the rapidity of uptake was apparent from the results obtained above.

Inspections of the treated branches at regular intervals, for signs of effect against the aphid populations, showed that the aphid population on the branches treated with Formulation 3 succumbed more rapidly than in the remaining treatments. The aphids were showing signs of toxicity 8–10 hours after application of the treatment with Formulation 3, compared to 24 hours for the remaining treatments.

The rapidity of insecticidal activity (rapidity of uptake in the tree) is important in limiting the transmission of insect borne viruses and diseases from infected insect populations (aphids, psylla) to the susceptible host plants. Accordingly, the quicker the mortality on insect pest (mites, thrip etc) the lower the resultant damage levels.

The choice of solvent in the formulation would thus in part influence the insecticidal efficacy of the formulation.

Where reference is made in the specification and claims to a "solvent" for the active ingredient, this term should be understood to mean a solvent in the true sense of the word, as well as a fluent or a dispersant.

Whenever reference is made in the specification and claims to an "aryl ethoxylate" as a preferred solvent, term should be understood to include also an alkyl aryl ethoxylate.

We claim:

1. A pesticidal formulation which is not phytotoxic when applied as a stem application to a trunk, branch or stem of a perennial plant or tree and which has systemic activity, said formulation comprising
   the compound methamidophos as an active ingredient;
   a non-volatile, non-phytoxic solvent for the active ingredient, which solvent is capable of penetrating at least the outer layers of the stem of the perennial plant or tree, and the solvent is selected from the group consisting of polyhydric alcohols, polyethylene glycol, aryl ethoxylates, ethoxylated propylene oxide polymers, and combinations thereof; and
   a colorant selected from the group consisting of dyes and pigments and being selected to impart an identifiable coloration to the formulation and to have a suitable solubility in water to be eluted from the formulation by atmospheric moisture over a period of time corresponding substantially to the duration of residual activity of the active ingredient.

2. The pesticidal formulation as claimed in claim 1, in which the colorant is an oil based dye.

3. The pesticidal formulation as claimed in claim 1, in which the active ingredient methamidophos is present in a concentration of between about 400 g/l and about 600 g/l based on the total volume of the formulation.

4. The pesticidal formulation as claimed in claim 1, in which the solvent is selected from the group consisting of glycerol, nonyl phenol ethoxylate, octyl phenol ethoxylate, hexylene glycol, ethoxylated propylene oxide polymer and polyethylene glycol.

5. The pesticidal formulation as claimed in 3, in which the solvent is selected from the group consisting of glycerol, nonyl phenol ethoxylate, octyl phenol ethoxylate, hexylene glycol, ethoxylated propylene oxide polymer and polyethylene glycol.

6. The pesticidal stem paint formulation according to claim 1 further comprising a substance capable of screening ultraviolet rays of the sun.

7. The pesticidal formulation as claimed in claim 1, which comprises as a further ingredient a substance capable of screening ultraviolet rays of the sun and selected from the group consisting of ethoxylated p-aminobenzoic acid, benzotriazole and benzophenone.

8. The pesticidal formulation as claimed in claim 7, in which the ultraviolet screening substance is ethoxylated p-aminobenzoic acid and is present in a quantity of between about 0.1% and 3% by weight of the total formulation.

9. The pesticidal formulation as claimed in claim 1 in which the non-volatile, non-phytoxic solvent is hexylene glycol.

10. The pesticidal formulation as claimed in claim 1, in the form of a stem paint for citrus trees, subtropical fruit trees, deciduous fruit trees, vines, and ornamental trees and shrubs, which comprises between about 400 g/l and about 600 g/l, based on the total volume of the formulation, of methamidopos as the active ingredient in a solvent selected from the group consisting of ethoxylated propylene oxide polymers, polyhydric alcohols, polyethylene glycol, aryl ethoxylates, and combinations thereof, and which comprises a colorant selected from the group consisting of dyes and pigments, said colorant selected to impart an identifiable coloration to the formulation and to have a suitable solubility in water to be eluted from the formulation by atmospheric moisture over a period of time corresponding substantially to the duration of residual activity of the active ingredient.

11. A pesticidal formulation as claimed in claim 10, in which the colorant is present in a quantity of between about 0.35% and 0.7% by weight of the total formulation.

12. A pesticidal formulation as claimed in claim 10, which comprises as a further ingredient a substance capable of screening ultraviolet rays of the sun and selected from the group consisting of ethoxylated p-aminobenzoic acid, benzotriazole and benzophenone.

13. A pesticidal formulation as claimed in claim 12, in which the ultraviolet screening substance is ethoxylated p-aminobenzoic acid and is present in a quantity of between about 0.1% and 3% by weight of the total formulation.

14. The pesticidal formulation according to claim 10 in which the solvent is hexylene glycol.

15. A method of combating pests on perennial plants and trees, which comprises the step of applying as a stem paint to a trunk, stem or branch of a perennial plant or tree a pesticidal formulation which is not phytotoxic to the trunk stem or branch and which has systemic activity, said composition comprising the compound methamidophos as an active ingredient and a non-volatile, non-phytotoxic solvent for the active ingredient, said active ingredient methamidophos being present in a concentration of between about 400 g/l and about 600 g/l based on the total volume of the formulation, said solvent being capable of penetrating the outer layers of the trunk, stem or branch of the perennial plant or tree, and said solvent selected from the group consisting of polyhydric alcohols, polyethylene glycol, aryl ethoxylates, ethoxylated propylene oxide polymers, and combinations thereof, and which formulation comprises a further ingredient in the form of a colorant selected from the group consisting of dyes and pigments and being selected to impart an identifiable coloration to the formulation and to have a suitable solubility in water to be eluted from the formulation by atmospheric moisture over a period of time corresponding substantially to the duration of residual activity of the active ingredient.

16. The method as claimed in claim 15, in which the formulation is applied in the form of a band encircling the trunk, stem or branch, the width of the band being approximately equal to the diameter of the trunk, stem or branch.

17. The method as claimed in claim 15, in which the formulation comprises as a further ingredient a substance capable of screening ultraviolet rays of the sun and selected from the group consisting of ethoxylated p-aminobenzoic acid, benzotriazole, and benzophenone.

18. The method according to claim 15 wherein the non-phytotoxic solvent is hexylene glycol.

19. A pesticidal stem paint formulation for application to a trunk, branch or stem of a perennial plant or tree, the formulation having systemic activity and consisting essentially of:

a first active ingredient being methamidophos, the first active ingredient having a residual activity for a period of time;

a second ingredient selected from the group consisting of polyhydric alcohols, polyethylene glycol, aryl ethoxylates, ethoxylated propylene oxide polymers, and combinations thereof, the second ingredient being present in a quantity to serve as a solvent for the first active ingredient; and a third ingredient, the third ingredient being a colorant selected from the group consisting of dyes and pigments, the colorant being selected to impart an identifiable coloration to the formulation, the colorant having a suitable solubility in water, the colorant being eluted from the formulation by atmospheric moisture over a period of time corresponding substantially to the period of time of the residual activity of the first active ingredient.

20. The pesticidal stem paint formulation as claimed in claim 19, wherein the first active ingredient is present in a concentration of between about 400 g/l and about 600 g/l based on the total volume of the formulation.

21. The pesticidal stem paint formulation as claimed in claim 19, wherein the second ingredient is selected from the group consisting of glycerol, nonyl phenol ethoxylate, octyl phenol ethoxylate, hexylene glycol, ethoxylated propylene oxide polymer and polyethylene glycol.

22. The pesticidal stem paint formulation as claimed in claim 20, wherein the second ingredient is selected from the group consisting of glycerol, nonyl phenol ethoxylate, octyl phenol ethoxylate, hexylene glycol, ethoxylated propylene oxide polymer and polyethylene glycol.

23. The pesticidal stem paint formulation as claimed in claim 19 wherein the colorant is present in a quantity of between about 0.35% and 0.7% by weight of the total formulation.

24. The pesticidal stem paint formulation as claimed in claim 20 wherein the colorant is present in a quantity of between about 0.35% and 0.7% by weight of the total formulation.

25. The pesticidal stem paint formulation as claimed in claim 22 wherein the colorant is present in a quantity of between about 0.35% and 0.7% by weight of the total formulation.

26. The pesticidal stem paint formulation as claimed in claim 19, wherein the second ingredient is hexylene glycol.

27. The pesticidal stem paint formulation is claimed in claim 20, wherein the second ingredient is hexylene glycol.

28. A method of combating pests on perennial plants and trees, the method comprising the step of applying the pesticidal formulation claimed in claim 19 as a stem paint to a trunk, stem, or branch of a perennial plant or tree.

29. A method of combating pests on perennial plants and trees, the method comprising the step of applying the pesticidal formulation claimed in claim 20 as a stem paint to a trunk, stem, or branch of a perennial plant or tree.

30. A method of combating pests on perennial plants and trees, the method comprising the step of applying the pesticidal formulation claimed in claim 19 in the form of a band encircling a trunk, stem or branch of a perennial plant or tree, the width of the band being approximately equal to a diameter of the trunk, stem or branch.

31. A method of combating pests on perennial plants and trees, the method comprising the step of applying the pesticidal formulation claimed in claim 20 in the form of a band encircling a trunk, stem or branch of a perennial plant or tree, the width of the band being approximately equal to a diameter of the trunk, stem or branch.

32. A method of combating pests on perennial plants and trees, the method comprising the step of applying the pesticidal formulation claimed in claim 22 in the form of a band encircling a trunk, stem or branch of a perennial plant or tree, the width of the band being approximately equal to a diameter of the trunk, stem or branch.

33. A pesticidal stem paint formulation for application to a trunk, branch or stem of a perennial plant or tree, the formulation having systemic activity and consisting essentially of:

a first active ingredient being methamidophos, the first active ingredient having residual activity for a period of time;

a second ingredient selected from the group consisting of polyhydric alcohols, aryl ethoxylates, polyethylene glycol, ethoxylated propylene oxide polymers, and combinations thereof, the second ingredient being present in a quantity to serve as a solvent for the first active ingredient;

a third ingredient, the third ingredient being a colorant selected from the group consisting of dyes and pigments, the colorant being selected to impart an identifiable coloration to the formulation, the colorant having a suitable solubility in water, the colorant being eluted from the formulation by atmospheric moisture over a period of time corresponding substantially to the period of time of the residual activity of the first active ingredient; and a fourth ingredient capable of screening ultraviolet rays of the sun.

34. The pesticidal stem paint formulation according to claim 33 wherein the fourth ingredient is selected from the group consisting of ethoxylated p-aminobenzoic acid, benzotriazole and benzophenone.

35. The pesticidal stem paint formulation as claimed in claim 34 wherein the first active ingredient is present in a concentration of between about 400 g/l and about 600 g/l based on the total volume of the formulation.

36. The pesticidal stem paint formulation as claimed in claim 33 wherein the second ingredient is selected from the group consisting of glycerol, nonyl phenol ethoxylate, octyl phenol ethoxylate, hexylene glycol, ethoxylated propylene oxide polymer, and polyethylene glycol.

37. The pesticidal stem paint formulation according to claim 36 wherein the fourth ingredient is selected from the group consisting of ethoxylated p-aminobenzoic acid, benzotriazole and benzophenone.

38. The pesticidal stem paint formulation as claimed in claim 33, in which the non-phytotoxic solvent is hexylene glycol.

39. The pesticidal stem paint formulation as claimed in claim 33, in which the colorant is present in a quantity of between about 0.35% and 0.7% by weight of the total formulation.

40. The pesticidal stem paint formulation as claimed in claim 34, in which the non-phytotoxic solvent is hexylene glycol.

41. A pesticidal stem paint formulation as claimed in claim 34, in which the colorant is present in a quantity of between about 0.35% and 0.7% by weight of the total formulation.

42. A pesticidal stem paint formulation as claimed in claim 35, in which the non-phytotoxic solvent is hexylene glycol.

43. A pesticidal stem paint formulation as claimed in claim 35, in which the colorant is present in a quantity of between about 0.35% and 0.7% by weight of the total formulation.

44. A pesticidal stem paint formulation as claimed in claim 36, in which the non-phytotoxic solvent is hexylene glycol.

45. A pesticidal stem paint formulation as claimed in claim 36, in which the colorant is present in a quantity of between about 0.35% and 0.7% by weight of the total formulation.

46. A method of combating pests on perennial plants and trees, the method the step of applying the pesticidal formulation claimed in claim 33 as a stem paint to a trunk, stem, or branch of a perennial plant or tree.

* * * * *